United States Patent
Yarkoni et al.

(10) Patent No.: US 12,156,728 B2
(45) Date of Patent: *Dec. 3, 2024

(54) SYSTEMS AND METHOD FOR SCANNING SUBJECTS TO ASCERTAIN BODY MEASUREMENTS

(71) Applicant: VAYYAR IMAGING LTD., Yehud (IL)

(72) Inventors: Noam Sol Yarkoni, Ramat Gan (IL); Shay Moshe, Petach Tikva (IL); Iddo Bar-David, Talmei Elazar (IL); Eyal Koren, Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/110,426

(22) Filed: Feb. 16, 2023

(65) Prior Publication Data
US 2023/0200680 A1   Jun. 29, 2023

Related U.S. Application Data

(63) Continuation of application No. 17/631,507, filed as application No. PCT/IB2020/062121 on Dec. 17, 2020, now Pat. No. 11,607,151.

(60) Provisional application No. 62/955,482, filed on Dec. 31, 2019, provisional application No. 62/948,825, filed on Dec. 17, 2019.

(51) Int. Cl.
*A61B 5/107* (2006.01)
*A61B 5/05* (2021.01)
*G01S 13/00* (2006.01)

(52) U.S. Cl.
CPC ............ *A61B 5/107* (2013.01); *A61B 5/05* (2013.01); *G01S 13/003* (2013.01)

(58) Field of Classification Search
None
See application file for complete search history.

(56) References Cited

U.S. PATENT DOCUMENTS

| | | | |
|---|---|---|---|
| 2002/0075178 A1* | 6/2002 | Woodington | G01S 13/87 342/195 |
| 2014/0350815 A1* | 11/2014 | Kambe | B60W 30/0956 701/70 |
| 2015/0285901 A1 | 10/2015 | Rose | |
| 2016/0223647 A1 | 8/2016 | Nichols et al. | |
| 2016/0253807 A1* | 9/2016 | Jones | G06T 7/75 382/154 |
| 2018/0348343 A1* | 12/2018 | Achour | H01Q 1/364 |
| 2019/0361090 A1* | 11/2019 | Ochiai | G01S 7/03 |

* cited by examiner

*Primary Examiner* — Yi-Shan Yang
(74) *Attorney, Agent, or Firm* — AlphaPatent Associates Ltd.; Daniel J. Swirsky

(57) ABSTRACT

Systems and methods for performing body scans to ascertain body measurements of a subject. A radar based scanner may be used to generate a three dimensional image of a subject as a point cloud map of electromagnetic radiation reflected from a target region. The point cloud may be mapped to a parametric model of a standard human shape. The mapping may be optimized by adjusting parameters of the parametric model. The resulting parameters of the optimized model may be used to indicate the body measurements of the scanned subject.

15 Claims, 6 Drawing Sheets

SYSTEMS AND METHOD FOR SCANNING SUBJECTS TO ASCERTAIN BODY MEASUREMENTS

CROSS-REFERENCE TO RELATED APPLICATIONS

This application is a continuation of U.S. patent application Ser. No. 17/631,507 which was filed on Jan. 31, 2022 as a U.S. National Phase Application under 35 U.S.C. 371 of International Application No. PCT/IB62020/062121, which has an international filing date of Dec. 17, 2020, which claims the benefit of priority from U.S. Provisional Patent Application No. 62/948,825, filed Dec. 17, 2019, and U.S. Provisional Patent Application No. 62/955,482, filed Dec. 31, 2019, the contents of which are incorporated by reference in their entirety.

FIELD AND BACKGROUND OF THE DISCLOSURE

The disclosure herein relates to systems and methods for performing body scans. In particular, the disclosure relates to using a radar scanner to ascertain body measurements of a subject. The disclosure herein relates to systems and methods for monitoring soap dispensers. In particular, the disclosure relates to the monitoring of level of contents of liquid soap dispensers.

SUMMARY OF THE EMBODIMENTS

According to one aspect of the presently disclosed subject matter, a system is introduced for scanning the body of a subject. The system may comprise: a radar unit comprising, a preprocessor unit, and a processor unit. The radar unit may include at least one transmitter unit connected to an oscillator and configured to transmit electromagnetic waves into a monitored region, and at least one receiver unit configured to receive electromagnetic waves reflected by objects within the monitored region and operable to generate raw data. The preprocessor unit may be configured and operable to receive the raw data from the at least one receiver unit and operable to generate filtered point cloud data. The processor unit may have a memory unit, be configured to receive the filtered point cloud data from the preprocessor, and operable to compare the filtered point cloud with a human parametric model stored in a memory unit.

Optionally, the preprocessor unit comprises an amplitude filter operable to generate filtered data by selecting from the raw data voxels having amplitudes above a required threshold. Where appropriate, the preprocessor unit comprises a voxel selector operable to further reduce voxel number in the filtered data thereby generating the point cloud data. Variously, the voxel selector is operable to sample the filtered data and/or to cluster neighboring voxels. Accordingly, the amplitude may be further operable to set the value of each voxel having an amplitude above the required threshold to ONE, and the value of each voxel having an amplitude below the required threshold to ZERO.

Where appropriate, the processor further comprises an optimizer configured and operable to compare positions of each voxel in the human parametric model with positions of each voxel in the filtered point cloud. Optionally, the processor further comprises a parameter selector configured to receive comparison results from the optimizer and operable to generate a new candidate parametric model by adjusting parameters accordingly.

Variously, the radar unit may be embedded behind a surface transparent to radio waves, such as in at least one of a group comprising: a wall, a mirror frame, a window, under the floor, in a ceiling, an optical mirror.

According to one aspect of the presently disclosed subject matter, a method is taught for scanning the body of a subject. Such a method may include: providing at least one radar unit comprising at least one transmitter unit connected to an oscillator, and at least one receiver unit configured to receive electromagnetic waves; providing at least one processor unit configured to generate a parametric model of the subject; storing at least one parametric human model in a memory unit; transmitting electromagnetic waves into a monitored region; receiving electromagnetic waves reflected from objects in the monitored region; generating an amplitude matrix; generating a filtered point cloud; and comparing the filtered point cloud with the parametric human model.

Where appropriate, the method further includes sending the amplitude matrix to a preprocessing unit.

Optionally, the step of generating filtered point cloud comprises: determining a required threshold amplitude; receiving raw data from the receiver unit; and selecting raw data voxels having amplitudes above the required threshold. Accordingly, the step of generating a filtered point cloud may further comprise sampling filtered data and selecting voxels. Additionally or alternatively, the step of generating a filtered point cloud further may comprise clustering neighboring voxels Where appropriate, the step of generating a filtered point cloud further comprises setting the value of each voxel having an amplitude above the required threshold to ONE, and setting the value of each voxel having an amplitude below the required threshold to ZERO.

Additionally or alternatively, the step of generating a filtered point cloud may further comprise downsampling voxels and/or removing outlying data, Where appropriate, optimizing parameters of the parameteric model of the subject, for example by selecting initial parameters of for an initial model; comparing the filtered point cloud with the initial model; and adjusting parameters of the initial model accordingly.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings.

DETAILED DESCRIPTION

Figure 1:
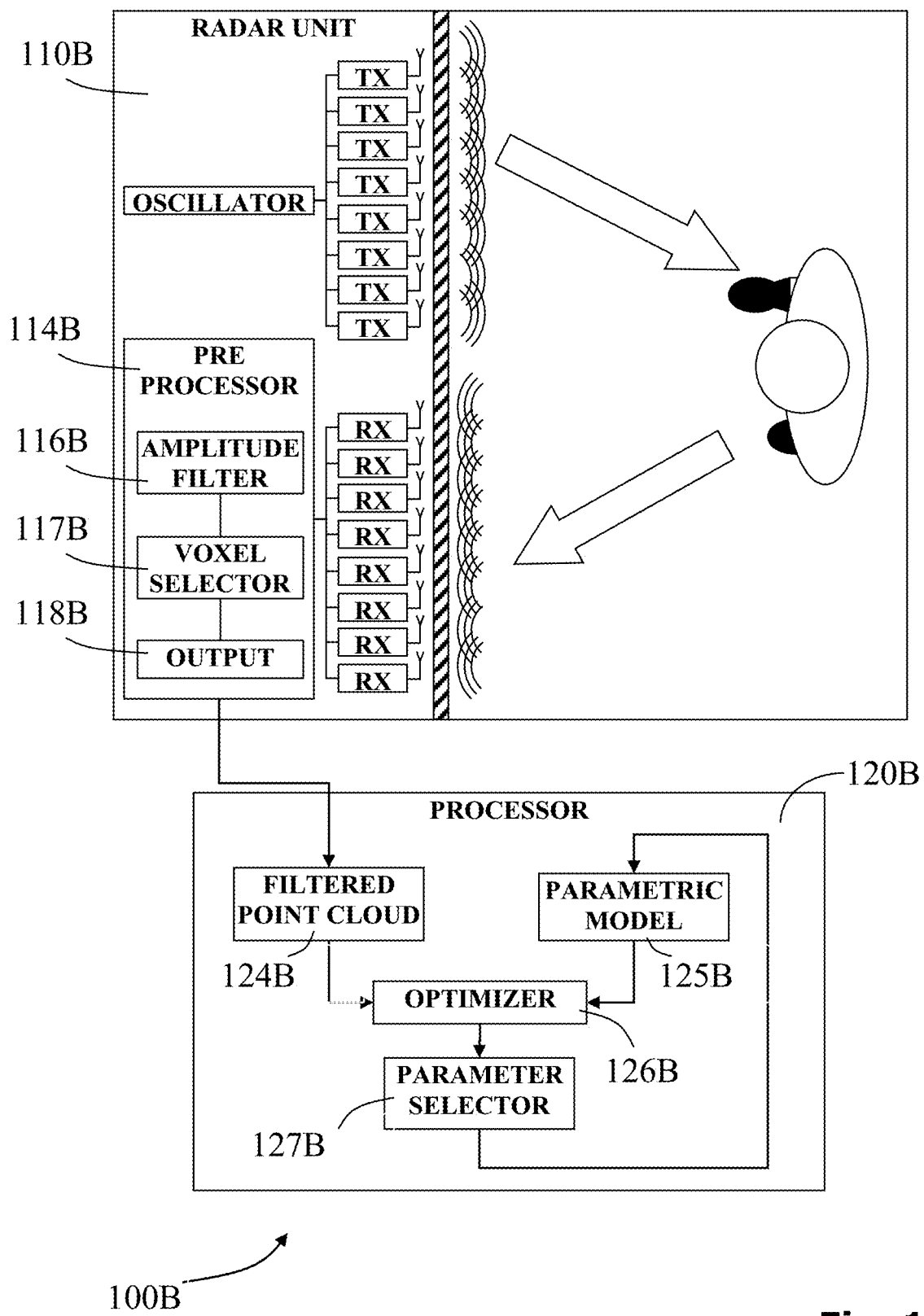
FIG. 1 is a schematic block diagram indicating selected components of a radar based body scanning system of the disclosure.

Aspects of the present disclosure relate to systems and methods for performing body scans to ascertain body measurements of a subject. A radar based scanner may be used to generate a three dimensional image of a subject as a point cloud map of electromagnetic radiation reflected from a target region. The point cloud may be mapped to a parametric model of a standard human shape. The mapping may be optimized by adjusting parameters of the parametric model. The resulting parameters of the optimized model may be used to indicate the body measurements of the scanned subject.

Other aspects of the present disclosure relate to systems and methods for ascertaining size, shape and volume of inanimate objects, and in particular to monitoring the content of a liquid in a vessel, either from within the vessel, or through electromagnetically penetrable walls of a vessel. In particular, radar-based scanners may be used to monitor the height level of the contents of liquid soap dispensers.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As appropriate, in various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials described herein for illustrative purposes only. The materials, methods, and examples not intended to be necessarily limiting. Accordingly, various embodiments may omit, substitute, or add various procedures or components as appropriate. For instance, the methods may be performed in an order different from described, and that various steps may be added, omitted or combined. In addition, aspects and components described with respect to certain embodiments may be combined in various other embodiments.

Referring now to FIG. 1, a schematic block diagram indicates selected components of a radar based body scanning embodiment of the system 100B. The radar based body scanning system 100B includes a radar unit 110B, and a processor 120B.

The radar unit 110B of the body scanning embodiment may be mounted to a wall for example behind an optical mirror transparent to radio waves, embedded in the frame of a mirror, or the like where it may scan a target region in front of the wall. The radar typically includes at least one array of radio frequency transmitter antennas and at least one array of radio frequency receiver antennas. The radio frequency transmitter antennas are connected to an oscillator (radio frequency signal source) and are configured and operable to transmit electromagnetic waves towards the target region. The radio frequency receiver antennas are configured to receive electromagnetic waves reflected back from objects within the target region.

The raw data generated by the receivers is typically a set of magnitude and phase measurements corresponding to the waves scattered back from the objects in front of the array. Spatial reconstruction processing is applied to the measurements to reconstruct the amplitude (scattering strength) at the three dimensional coordinates of interest within the target region. Thus each three dimensional section of the volume within the target region may represented by a voxel defined by four values corresponding to an x-coordinate, a y-coordinate, a z-coordinate, and an amplitude value.

Typically the receivers are connected to a pre-processing unit 114B configured and operable to process the amplitude matrix of raw data generated by the receivers and produce a filtered point cloud suitable for model optimization.

Accordingly, where appropriate, a preprocessing unit 114B may include an amplitude filter 116B operable to select voxels having amplitude above a required threshold and a voxel selector 117B operable to reduce the number of voxels in the filtered data, for example by sampling the data or clustering neighboring voxels. In this manner the filtered point cloud may be output 118B to a processor 120B. It is further note that the filtered point cloud may further be simplified by setting the amplitude value of each voxel to ONE when the amplitude is above the threshold and to ZERO when the amplitude is below the threshold.

The processor 120B which is in communication with the output 118B of the preprocessor unit 114B is operable to receive the filtered point cloud 124B from the output of the preprocessor 114B and to compare the filtered point cloud with a human parametric model 125B stored in a memory unit.

The parametric model 125B may be generated by averaging scans of multiple subjects and/or applying machine learning to such scans and stored in the memory unit of the processor or remotely. The parametric model may be represented as a model function which receives a set of values representing model parameters and returns as set of voxels which model the subject.

By way of example, parameters may be selected from various measurable values of a subject, for example for a human subject parameters such as gender, height, weight, waist size, inner-thigh, inseam, arm-span, hand span, wrist to shoulder length, shoe size and the like as well as combinations thereof may generate candidate models with characteristic voxel sets. In some examples, separate parametric models may be provided for male and female subjects.

Accordingly, the processor 120B may further include an optimizer 126B and a parameter selector 127B. The optimizer 126B may further be configured and operable to compare the positions of each voxel in the parametric model 125B with each voxel in the filtered point cloud 124B. The parameter selector 127B may be operable to receive the results of the comparison and to adjust the parameters accordingly so as generate a new candidate model. Once the optimizer 126B reaches an optimal model wherein no further adjustment significantly improves the candidate model, that candidate model may be selected as the best fit model of the scanned subject.

The subject may itself be characterized by the measurements used as parameter values for generating the best fit model.

Variously, the scanning arrangement may be embedded in a wall, a mirror frame, a window, under the floor, in a ceiling, behind an optical mirror transparent to radio waves or the like as required.

Additionally or alternatively the scanning arrangement itself be directed towards a mirror surface and may be configured and operable to extend the target region into the virtual reflected region inside the mirror. Accordingly, shielded or eclipsed regions of the subject may be rendered visible by reflection within the mirror.

Figure 2C:
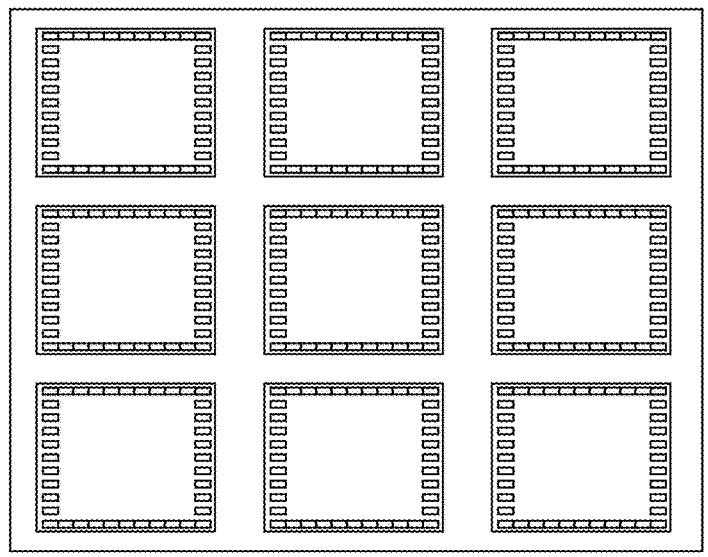
FIGS. 2A-C schematically illustrate various possible radar scanning arrangement for use with the radar based body scanning system of the disclosure.
Figure 2B:
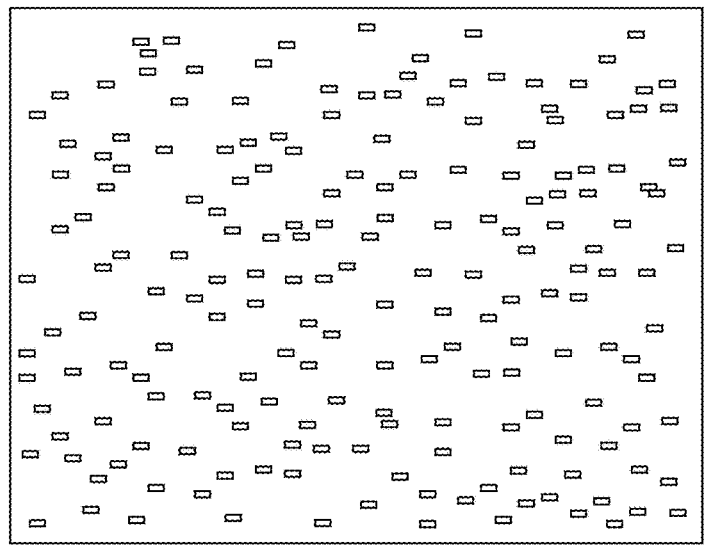
Figure 2A:
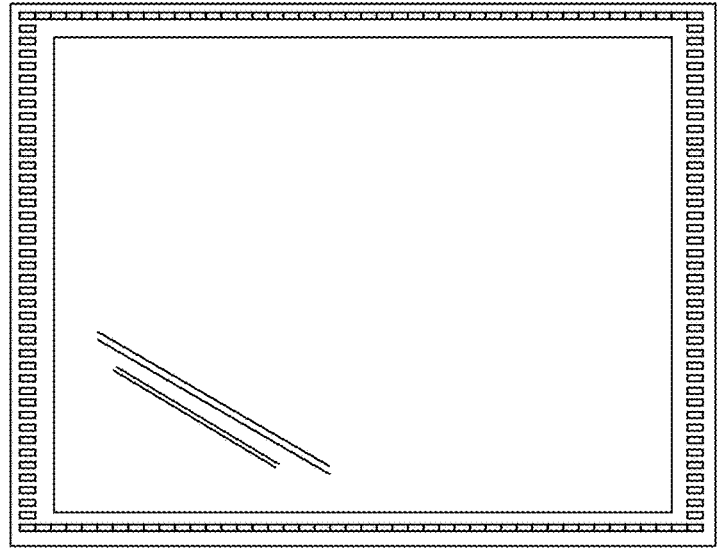

Referring now to FIGS. 2A-C, various possible radar scanning arrangements may be used with the radar based body scanning system of the disclosure. In particular, with reference to FIG. 2A, the scanning arrangement may include a rectangular array of transmitter and receiver antennas. Such an arrangement may, for example, be incorporated into the frame of a mirror or the like. Accordingly, a subject may be scanned and measured while viewing themselves in the mirror. Further, as illustrated in FIG. 2B, the antennas may be embedded in a pseudorandomly scattered array of receivers and transmitters which may be networked and controlled centrally.

With reference now to FIG. 2C, another possible radar scanning arrangement for use with the radar based body scanning system of the disclosure may include a set of nine radar scanning boards arranged in a square of three rows and three columns Each radar scanning boards may include a pair of linear array transmitter antennas and an orthogonally orientated pair of linear array receiver antennas. Although each scanning board may be controlled by dedicated controller chips and oscillators, these may be networked such that the set of scanning boards operate as a common unit generating a single set of raw amplitude data for the target region.

Figure 3:
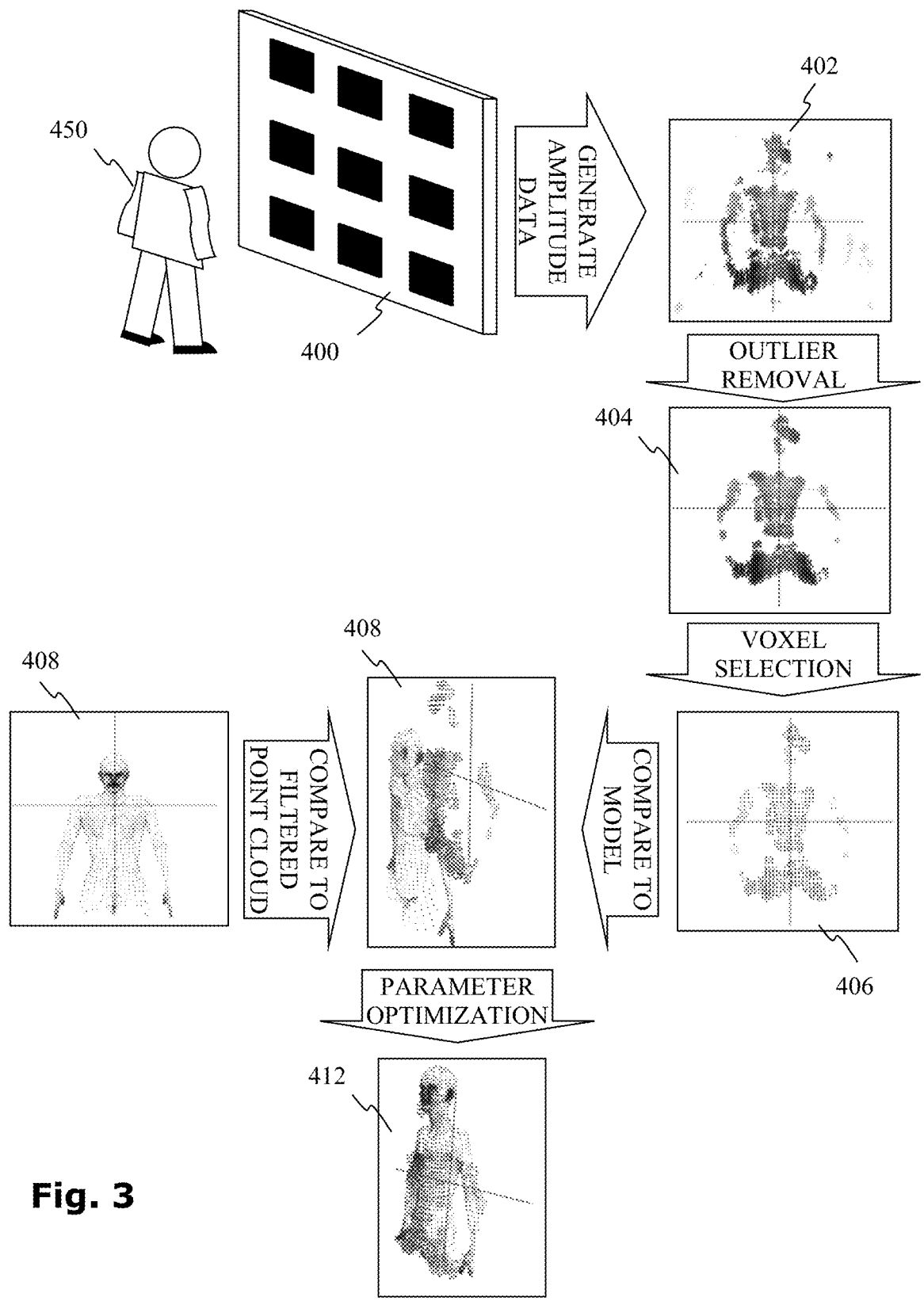
FIG. 3 is a schematic illustration of a possible data flow within a radar based body scanning system of the disclosure.

Referring now to FIG. 3, a schematic illustration is presented to show a possible data flow within the radar based body scanning system of the disclosure. A subject 450 stands in a target region in front of a radar scanning arrangement 400 such as described herein. The scanning arrangement generates a set of raw data representing a three dimensional amplitude map 402 indicating objects within the region including the subject. The three dimensional amplitude matrix 402 may be filtered by removing outlying voxels which are unconnected with the subject. The clean map 404 may be further sampled to select only a subset of voxels 406 such that a filtered amplitude map of the subject may be compared with a candidate parametric model 408. A candidate model 410 is thus constructed which may then be optimized to generate the best fit model 412.

Figure 4:
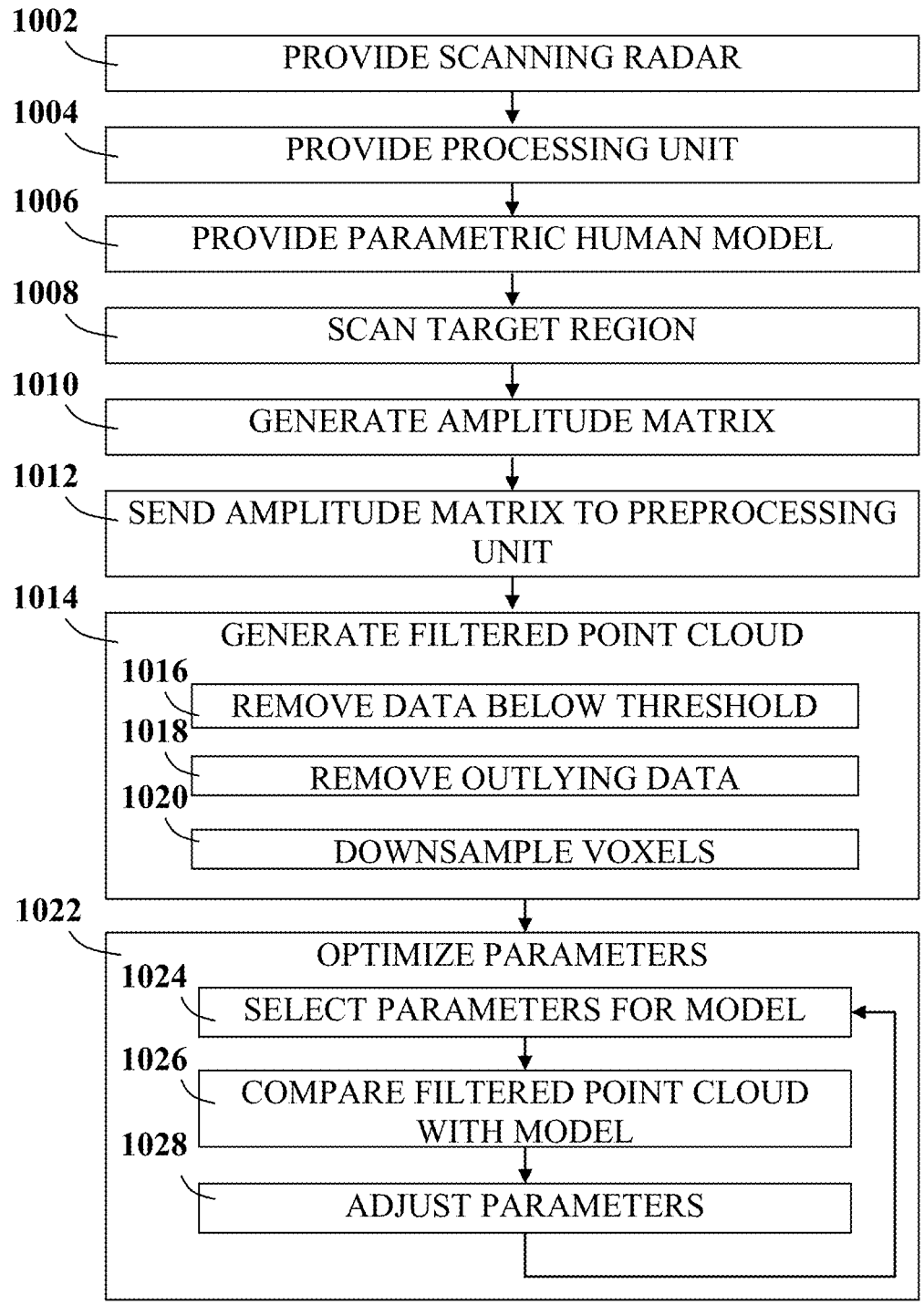
FIG. 4 is a flow diagram illustrating a method for scanning body of a subject and ascertaining body measurement of a subject using a radar based body scanning system of the disclosure.

Referring now to FIG. 4 is a flow diagram illustrating a method for scanning body of a subject and ascertaining body measurement of a subject using a radar based body scanning system of the disclosure.

The method incudes, providing a scanning radar 1002, providing a processing unit 1004, and providing a parametric human model 1006.

The scanning arrangement may scan a subject may be in the target region in front of the array 1008, thereby generating amplitude data for the region 1010.

The amplitude matrix is sent to a preprocessing unit 1012, which generates a filtered point cloud 1014. Optionally, the data may be processed by removing data below a threshold amplitude value 1016, removing outlying data 1018 and downsampling voxels 1020.

The resulting point cloud may be sent to a processor where a model is optimized 1022 for example by selecting a candidate set of parameters 1024, comparing the point cloud with the candidate model 1026, adjusting parameters 1028 and repeating until no further improvements are made.

It is particularly note that the output of the scanning device is a three dimensional point cloud. However, some of the regions of the point cloud may be missing from the scan for example due to shielding effects or regions at angles with poor coverage. Various compensation techniques may be used to interpolate for the missing data such as local averaging or the like.

Various optimization processes may be used for example, defining an objective function, comparing the candidate parametric model with the scanned point cloud, identifying which voxels in the candidate parametric model are geometrically closest to corresponding points in the point cloud, and calculating the Euclidean distance $\Delta$ between these points as given by:

$$\Delta = \sqrt{(x-x_m)^2 + (y-y_m)^2 + (z-z_m)^2}$$

where x is the x-coordinate of the point in the point cloud, $x_m$ is the x-coordinate of the closest point in the candidate parametric model, y is the y-coordinate of the point in the point cloud, $y_m$ is the y-coordinate of the closest point in the candidate parametric model, z is the z-coordinate of the point in the point cloud, and $z_m$ is the z-coordinate of the closest point in the candidate parametric model.

The value of the sum of all the Euclidean distances $\Sigma \Delta_i$ may be minimized by various optimization algorithms, such as Sequential Least Squares Quadratic Programming (SLSQP) for example. In this way the optimal parameters may be selected for the human parametric model. Other optimization methods will occur to those skilled in the art.

The generated best fit model may be used to find full body measurements even from missing parts in the scan and potentially of body parts that haven't been scanned at all.

Well stocked soap dispensers are essential to the sanitation of public services. However, ensuring that the soap dispensers do not run out requires frequent inspection of dispensers which often difficult to access. Such inspection is time consuming, costly and labor intensive. There is, therefore, for a need for a cost effective system and method for automating the monitoring of contents of soap dispensers.

Figures 5A, 5B, 5C:
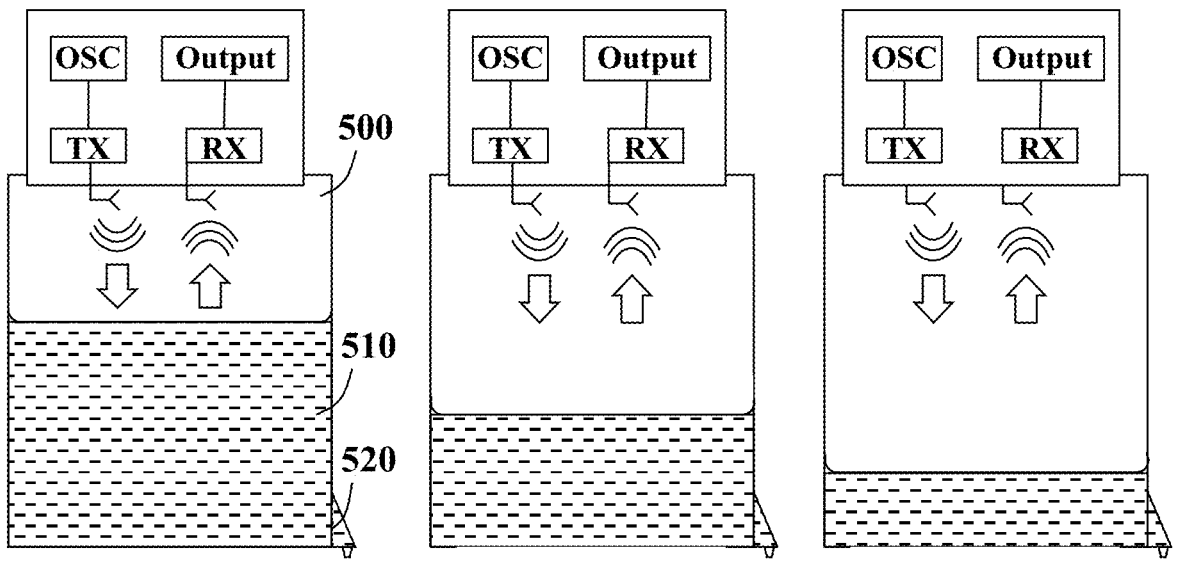
FIGS. 5A-C are schematic representations of an embodiment of a system for monitoring the level of a soap dispenser.

Referring now to FIG. 5A, a schematic representation is shown of an embodiment of a system for monitoring the level of a liquid in a soap dispenser 500.

The soap dispenser 500 of the example includes a soap reservoir 510 and a dispensing nozzle 520. Other soap dispensers will occur to those skilled in the art. It is a particular feature of such soap dispensers that the reservoir includes a container for containing a volume of soap the height of the soap contents indicates the volume of soap remaining in the reservoir.

Typically the height of the soap has been periodically inspected manually to ascertain the contents of the soap dispenser and to decide whether the soap needs to be replaced or replenished.

In order to automate the contents inspection, the soap reservoir of the invention includes a monitoring system configured and operable to monitor the level of the soap reservoir. The monitoring system may comprise a radar chip including a transmitter, a receiver, a controller and an output mechanism.

The transmitter may include an oscillator connected to at least one transmitter antenna or an array of transmitter antennas and configured to produce a beam of electromagnetic radiation, such as microwave radiation or the like, directed towards the surface of the soap reservoir.

The receiver may include at least one receiving antenna or array of receiver antennas configured and operable to receive electromagnetic radiation. Typically a processor is provided to identify reflected radiation received by the receiver which having the characteristic frequency of the transmitted beam. It is a particular feature of the current disclosure that the receiver further includes a timer for timing received signals.

Accordingly, radiation directed towards the surface of the soap reservoir may be reflected back from the surface and received by the receiver. Because electromagnetic radiation travels at a fixed speed, the distance from the monitor to the surface of the soap reservoir may be calculated by measuring the time taken for a transmitted beam to be received back by the receiver.

Figure 6A:
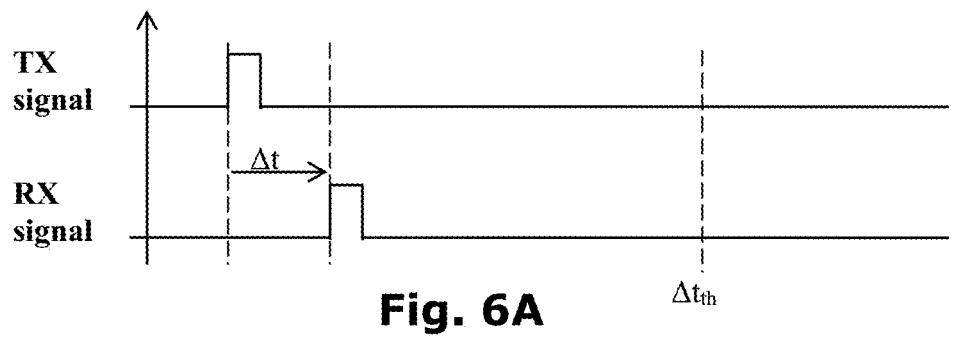
FIGS. 6A-C are a set of corresponding graphs indicating the transmitted and received wave signals for the monitoring system indicating different content levels of the dispensers.

Referring to the graph of FIG. 6A, a corresponding graph is presenting indicating the transmitted and received wave signals for the monitoring system indicating a well stocked soap dispenser.

It is noted that there is a measurable time interval $\Delta t$ between the transmitted signal TX and the received signal RX. The volume V of the soap reservoir relates to the time interval according to the formula:

$$V = A(H - c\Delta t)$$

where A is the area of the base of the reservoir, H is the height from the base of the reservoir to the monitor antennas and c is the speed of transmitted radiation (typically the speed of electromagnetic radiation through air).

Accordingly, the longer the time interval $\Delta t$ the lower the level of the soap.

Figure 6B:
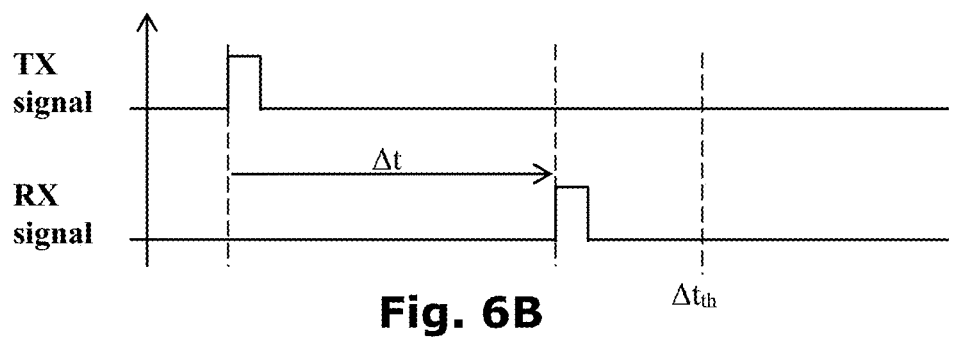

Referring now to FIG. 5B, a soap dispenser is schematically represented in which the level is lower than in FIG. 5A. Such a soap dispenser may not require immediate replenishment. FIG. 6B shows the corresponding response graph for the monitor in which the time interval $\Delta t$ is longer than in FIG. 6A indicating that the soap level is reduced.

Figure 6C:
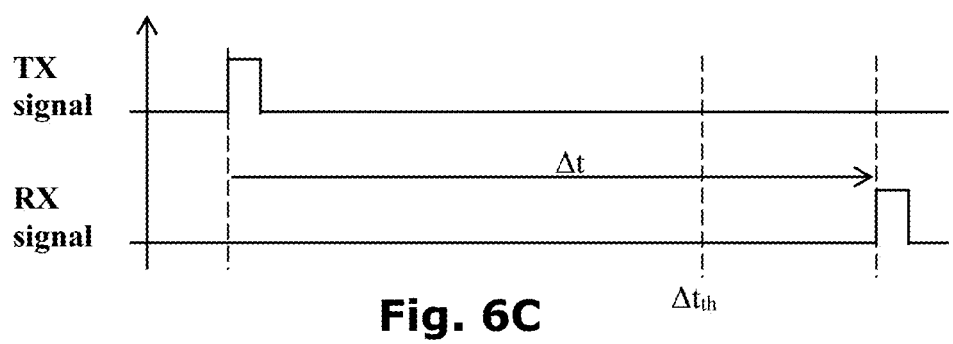

Referring now to FIG. 5C, another soap dispenser is schematically represented in which the level has dropped below a threshold requiring replenishment. FIG. 6C shows the corresponding response graph for the monitor in which the time interval $\Delta t$ is longer than the threshold time interval $\Delta t_{th}$ thereby indicating that the soap will need to be replenished.

Figure 7:
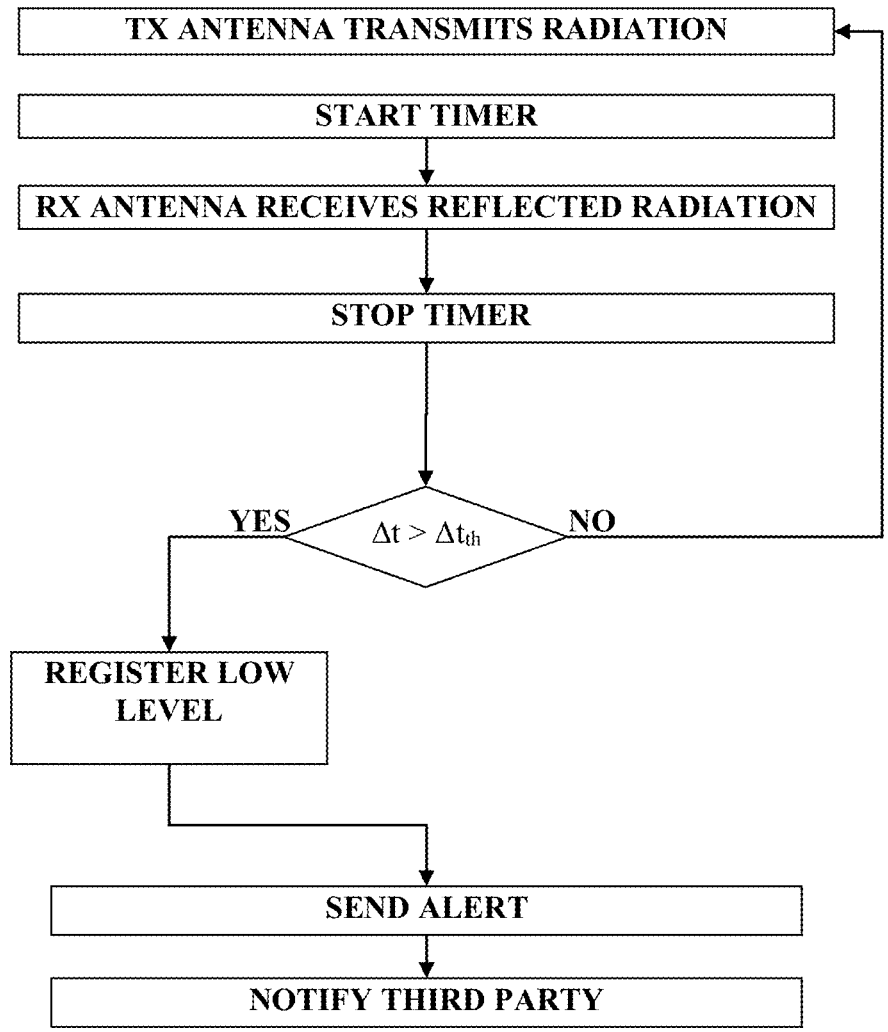
FIG. 7 is a flowchart illustrating a possible method for monitoring soap dispensers.

Reference is now made to the flowchart of FIG. 7 which illustrates a possible method for monitoring soap dispensers.

The transmitter transmits radiation in the general direction of the surface of the soap reservoir. As the signal is transmitted a timer is started.

A reflected signal is received by the receiver antenna. As soon as the reflected signal is received, the timer is stopped.

The controller or processor may then compare the measured time interval $\Delta t$ with the threshold time interval $\Delta t_{th}$. Where the measured time interval $\Delta t$ is shorter than the threshold time interval $\Delta t_{th}$ the system may repeat the first steps. Where the measured time interval $\Delta t$ exceeds the threshold time interval $\Delta t_{th}$ the system may register a low soap level event.

The radar can be located outside the container and inspect the level of the soap through a dielectric wall or cover. By this the chances that the radar components are stained by soap is reduced.

Another embodiment of the invention comprises an imaging radar, such as MIMO radar comprising multiple transmit and receive antennas so as to obtain spatial resolution. Such radar can observe the soap container from the side, being completely outside the container. The method takes advantage from the fact that soap containers are typically made of dielectric material, such as plastic, glass or ceramics. The reflectivity of the wall which is in contact with the soap (or other liquid, for that purpose) is different from the reflectivity of the wall which is backed by air (above the level of the liquid). By producing an image of reflectivity versus height, the level of soap can be detected. The volume of the liquid may be further estimated using a parametric model of the container an its cross-section.

Various actions may be triggered by the low soap level event, such as turning on a warning light, a warning signal or the like. Further, where the system includes a communication unit, the unit may be operable to send an alert, notify a third party for example a caretaker, orderly, janitor, sanitary officer or the like such that appropriate action may be taken. Still other alert responses may occur to those skilled in the art.

It is appreciated that certain features of the invention, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the invention has been described in conjunction with specific embodiments thereof, it is evident that other alternatives, modifications, variations and equivalents will be apparent to those skilled in the art. Accordingly, it is intended to embrace all such alternatives, modifications, variations and equivalents that fall within the spirit of the invention and the broad scope of the appended claims. Additionally, the various embodiments set forth hereinabove are described in terms of exemplary block diagrams, flow charts and other illustrations. As will be apparent to those of ordinary skill in the art, the illustrated embodiments and their various alternatives may be implemented without confinement to the illustrated examples. For example, a block diagram and the accompanying description should not be construed as mandating a particular architecture, layout or configuration.

Technical Notes

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The scope of the disclosed subject matter is defined by the appended claims and includes both combinations and sub combinations of the various features described hereinabove as well as variations and modifications thereof, which would occur to persons skilled in the art upon reading the foregoing description.

What is claimed is:

1. A system for scanning the body of a subject, the system comprising:
    a radar unit comprising:
        at least one transmitter unit connected to an oscillator and configured to transmit electromagnetic waves into a monitored region, and
        at least one receiver unit configured to receive electromagnetic waves reflected by objects within the monitored region and operable to generate raw data;
    a preprocessor unit configured and operable to receive the raw data from the at least one receiver unit and operable to reduce number of voxel of data and thereby to generate a filtered point cloud data; and
    a processor unit having a memory unit and configured to receive the filtered point cloud data from the preprocessor unit and operable to generate a comparison between the filtered point cloud data with a human parametric model stored in a memory unit,
    wherein the processor further comprises a parameter selector configured to generate a new candidate parametric model by adjusting parameters of the human parametric model according to the comparison between the filtered point cloud data and an initial model, and
    wherein the preprocessor unit comprises an amplitude filter operable to generate filtered point cloud data by selecting from raw data voxels having amplitudes above a required threshold.

2. The system of claim 1 wherein the preprocessor unit comprises a voxel selector operable to further reduce voxel number in the filtered data thereby generating the filtered point cloud data.

3. The system of claim 1 wherein the voxel selector is operable to sample the filtered data.

4. The system of claim 1 wherein the voxel selector is operable to cluster neighboring voxels.

5. The system of claim 1 wherein the amplitude filter is further operable to set a value of each voxel of the raw data voxels having an amplitude above the required threshold to one, and a value of each voxel of the raw data voxels having an amplitude below the required threshold to zero.

6. The system of claim 1 wherein the radar unit is embedded behind a surface transparent to radio waves.

7. The system of claim 1 wherein the radar unit is embedded in at least one of a group comprising: a wall, a mirror frame, a window, under a floor, in a ceiling, an optical mirror.

8. A system for scanning the body of a subject, the system comprising:
- a radar unit comprising:
  - at least one transmitter unit connected to an oscillator and configured to transmit electromagnetic waves into a monitored region, and
  - at least one receiver unit configured to receive electromagnetic waves reflected by objects within the monitored region and operable to generate raw data;
- a preprocessor unit configured and operable to receive the raw data from the at least one receiver unit and operable to reduce number of voxel of data and thereby to generate a filtered point cloud data; and
- a processor unit having a memory unit and configured to receive the filtered point cloud data from the preprocessor unit and operable to generate a comparison between the filtered point cloud data with a human parametric model stored in a memory unit,
- wherein the processor further comprises a parameter selector configured to generate a new candidate parametric model by adjusting parameters of the human parametric model according to the comparison between the filtered point cloud data and an initial model, and
- wherein the processor unit further comprises an optimizer configured and operable to compare positions of each point in the human parametric model with positions of each voxel in the filtered point cloud data.

9. A method for scanning the body of a subject comprising:
- providing at least one radar unit comprising at least one transmitter unit connected to an oscillator, and at least one receiver unit configured to receive electromagnetic waves;
- providing at least one processor unit configured to generate at least one human parametric model of the subject;
- storing the at least one human parametric model in a memory unit; transmitting the electromagnetic waves into a monitored region;
- receiving the electromagnetic waves reflected from objects in the monitored region;
- generating an amplitude matrix of raw data generated by the receivers; processing the amplitude matrix and to generate a filtered point cloud by:
  - determining a required threshold amplitude;
  - receiving raw data from the receiver unit;
  - selecting raw data voxels having amplitudes above the required threshold; and
  - comparing the filtered point cloud with the at least one human parametric human model.

10. The method of claim 9 further comprising sending the amplitude matrix to a preprocessing unit.

11. The method of claim 9 wherein the step of generating the filtered point cloud further comprises sampling filtered data and selecting voxels.

12. The method of claim 9 wherein the step of generating the filtered point cloud further comprises setting a value of each voxel of the raw data voxels having an amplitude above the required threshold to one, and setting a value of each voxel of the raw data voxels having an amplitude below the required threshold to zero.

13. The method of claim 9 wherein the step of generating the filtered point cloud further comprises downsampling voxels.

14. The method of claim 9 wherein the step of generating the filtered point cloud further comprises removing outlying data.

15. The method of claim 9 further comprising optimizing parameters of the at least one human parametric model of the subject.

* * * * *